United States Patent [19]
Hemmilä et al.

[11] Patent Number: 5,637,509
[45] Date of Patent: Jun. 10, 1997

[54] MODULATED HOMOGENEOUS FLUORESCENCE BIOSPECIFIC AFFINITY ASSAY EMPLOYING FLUORESCING LANTHANIDE CHELATES AS COVALENT LABELS

[75] Inventors: Ilkka Hemmilä; Timo Lövgren, both of Turku, Finland

[73] Assignee: Wallac Oy, Turku, Finland

[21] Appl. No.: 626,528

[22] Filed: Dec. 12, 1990

Related U.S. Application Data

[63] Continuation of Ser. No. 246,793, Sep. 20, 1988, abandoned.

[30] Foreign Application Priority Data

Sep. 24, 1987 [SE] Sweden ............... 8703682

[51] Int. Cl.⁶ ............... G01N 33/542; G01N 33/536; G01N 33/533; G01N 33/53
[52] U.S. Cl. ............... 436/537; 436/501; 436/536; 436/546; 436/547; 436/826
[58] Field of Search ............... 436/501, 536, 436/547, 546, 826, 537

[56] References Cited

U.S. PATENT DOCUMENTS

| | | | |
|---|---|---|---|
| 4,374,120 | 2/1983 | Soini | 436/546 |
| 4,454,232 | 6/1984 | Brealio et al. | 436/504 |
| 4,468,469 | 8/1984 | Atkinson et al. | 436/500 |
| 4,565,790 | 1/1986 | Hemmila | 436/537 |
| 4,587,223 | 5/1986 | Soini et al. | 436/546 X |
| 4,637,988 | 1/1987 | Hinshaw et al. | 436/546 |
| 4,734,378 | 3/1988 | Wang et al. | 436/175 |
| 4,751,190 | 6/1988 | Chiapetta et al. | 436/546 |
| 4,761,481 | 8/1988 | Hale et al. | 546/296 |
| 4,772,563 | 9/1988 | Evangelista et al. | 436/546 X |
| 4,808,541 | 2/1989 | Mikola et al. | 436/501 |
| 4,816,419 | 3/1989 | Halfman | 436/546 |
| 4,837,169 | 6/1989 | Toner | 436/546 |
| 4,857,475 | 8/1989 | Dakubu | 436/500 X |
| 4,920,195 | 4/1990 | Kankare et al. | 534/16 |
| 4,925,804 | 5/1990 | Hale et al. | 436/501 |

FOREIGN PATENT DOCUMENTS

| | | |
|---|---|---|
| 20103558 | 3/1984 | European Pat. Off. . |
| WO87/07955 | 6/1987 | WIPO . |

OTHER PUBLICATIONS

Dechand et al, "New Approach to Competitive Lanthanide Immunoassay . ." Clin. Chem. 34 (3), 501–504 (1988).
Analytical Biochemistry 137, 335–343 (1984) –Hemmila et al "Europium as a label in time–resolved immunofluorometric assays".

*Primary Examiner*—Michael P. Woodward
*Attorney, Agent, or Firm*—Lowe, Price, LeBlanc & Becker

[57] ABSTRACT

Method for a homogeneous biospecific affinity assay for determining the content of a substance (analyte) in a biological sample. The assay is carried out in an aqueous reaction medium by means of time-resolved fluorescence spectroscopy and with a biospecific affinity reactant labeled with a lanthanide chelate in which a lanthanide ion exhibiting ionic fluorescence is chelated by a ligand bound covalently to the reactant. The characteristic feature is (i) that the lanthanide chelate formed by the lanthanide ion together with the covalently bound ligand forms a fluorescent chelate, and (ii) that a modulator is added which stabilizes the lanthanide chelate so that the lanthanide fluorescence as measured from the medium becomes a practically pure function of the analyte concentration therein.

20 Claims, 5 Drawing Sheets

MODULATED HOMOGENEOUS FLUORESCENCE BIOSPECIFIC AFFINITY ASSAY EMPLOYING FLUORESCING LANTHANIDE CHELATES AS COVALENT LABELS

This is a continuation of application Ser. No. 07/246,793, filed Sept. 20, 1988 now abandoned and the benefits of 35 USC 120 are claimed relative to it.

TECHNICAL FIELD OF THE INVENTION AND PRIOR ART TECHNIQUE

The invention is concerned with a homogenous assay method of the type set forth above. The method utilizes time-resolved fluorescent spectroscopy in combination with a reactant labeled with a covalently bound lanthanide chelate. That portion of the chelate which chelates the lanthanide ion is called "ligand". The labeled reactant participates in a biospecific affinity reaction.

The invention is applicable to reactant pairs of vastly different types of biospecific affinity for each other. Usually this affinity is an immune-type affinity; the invention will therefore be described in the first place as an immunochemical assay method. This, of course, does not mean that one cannot use bioaffinity pairs of reactants other than antibody-antigen (hapten), like, for instance, protein A-Fc (IgG), carbohydrate structures-lectin, RF-immune complex, Clq-immune complex, hormone-receptor etc.

The term "immunochemical assay method" implies that a substance (analyte) is detected by means of an immune reaction between an analyte and its immunological counterpart. By utilizing an immune reactant having an indicatable group and by properly adjusting the reactants of the system it is possible to create conditions such that the said indicatable group will form part of the antigen-antibody complexes resulting from the immune reaction and the amount of complexed indicatable group will be a measure of the analyte occurrence in the reaction medium. By measuring the indicatable group either in the immunocomplexed form or in its free form it is possible to obtain a measure of the amount of analyte in the sample. Examples of reactants that can be provided with indicatable groups are antigens, haptens and antibodies.

It is a well-known phenomenon that the fluorescence properties of a marker group may be subject to changes due to the participation of the labeled immune reactant in an immune reaction. Within the field of fluorescence immunological testing, this phenomenon has prompted the development of homogeneous methods on one hand and heterogeneous methods on the other hand. Homogeneous methods comprise measuring the marker group signal from a labeled immune reactant that is homogeneously distributed in the reaction medium. This measuring step is not preceded by any physical separation of labeled immune reactant present in the immune complexes formed (=bound labeled reactant) from labeled immune reactant not present in the complexes (=free labeled reactant). In the case of the heterogeneous methods there is such a separation. It is well known that recourse may be had to various different reaction and incubation sequences. Examples of these are simultaneous additions (mixing) of the immune reactants or adding them in a predetermined order. Especially worth mentioning are inhibition methods (=competitive methods) where an analyte analog having an epitope in common with the analyte and provided with a detectable group is made to compete for an insufficient number of binding sites on the immunological counterpart of the analyte. Within the field of conventional homogeneous fluorescence immunological techniques, it has been previously known to employ so-called modulators, i.e. substances acting on the fluorescent signal in some such manner as to result in improved possibilities of analysis (Halfman and Jay, Clin. Chem. 32 (1986) 1677–81 and U.S. Pat. No. 4,640,898). For a general survey of fluorescence immunological methods see Hemmilä, I (Clin. Chem. 31 (1985) 359–70).

Lanthanide chelates in combination with time-resolved fluorescent spectroscopy have become a generally accepted immunochemical tool during the last ten years (Hemmilä, I, loc. cit.). From spectroscopic and quantum chemical data it was concluded that among the lanthanide ions the $Dy^{3+}$, $Sm^{3+}$, $Tb^{3+}$ and $Eu^{3+}$ are the most suitable ones because they exhibit ionic fluorescence whereas others like $La^{3+}$, $Gd^{3+}$ and $Lu^{3+}$ are totally unsuitable because they have no such fluorescence properties. In view of the predictable practical advantages it has been generally desired that the lanthanide chelates employed should exhibit a delayed fluorescence with decay times of more than 10 μs. Unfortunately, the lanthanide chelates available have stability constants (lit/mol) too low to be useful for assaying an analyte in such concentration ranges ($<10^{-4}M$) as are normal for immunochemical assay procedures. Another disadvantage of the known fluorescent chelates is the fact that their fluoresconce tends to be inhibited by water—which, of course, is always present in immunochemical assay procedures. This inhibition is due to the strong capacity of the lanthanide ions of co-ordinating water molecules so that absorbed light energy (excitation energy) is transferred to the solvent rather than being emitted as fluorescence. As in all kinds of fluorescent methods, the fluorescence signal from the lanthanide chelate is also affected by numerous substances that are often present in biological samples in amounts varying over a wide range. Depending on the substance and ligand, the half-life period of the fluorescence may be lengthened or shortened and the intensity of the fluorescence may be increased or decreased etc.

Within the field of heterogeneous immunochemical assays, the DELFIA® assay procedure (Wallac Oy, Turku, Finland) has solved the stability problem and water problem. In its form as described up to now, DELFIA® uses non-fluorescent lanthanide conjugates bound covalently to an immune reactant. In the DELFIA® procedure the lanthanide ion is released from its chelating ligand and is made to exhibit a fluorescence in an aqueous medium together with a developer consisting of (a) a detergent, (b) a chelating compound with which the lanthanide ion employed gives fluorescence and (c) a synergistic compound. The intensity of the fluorescence and half-life depend not only on the analyte but in addition on the pH, on the detergent, on the synergistic compound and on the chelating compound (see inter alia Halvarson et al., J. Chem. Phys. 41 (1964) pp 157 and 2752, and Hemmilä et al., Anal. Biochem. (1984) pp 335–343).

Up to the present date there is only a somewhat scanty literature dealing with homogeneous immunochemical methods which utilize time resolved fluorescence spectroscopy and lanthanide chelates. It has been shown, however, that the ligand field surrounding the lanthanide ion affects both the intensity and the lifetime of the fluorescence (Filipescu et al., J. Phys. Chem. 68 (1964) 3324; Crosby et al., J. Chem. Phys. 34 (1961) 743 and J. Phys. Chem. 66 (1962) 2493; and Lövgren et al., Alternative in Immunoassays, Ed.: Collins W P, John Wiley & Sons, Chichester (1985) 203). It may, therefore, be expected that the physical properties of fluorescent lanthanide chelates employed as marker groups in homogeneous immunochemical methods will potentially undergo changes consequential to an immune reaction. When the ligand field around the lanthanide ion brings about a change in energy absorption then the effects on properties which are relevant for energy transfer and emission will be predictable. This will affect the intensity and lifetime (half-life) of the lanthanide ion fluorescence. We have previously shown that the aforesaid assumption is correct, inasmuch as we have had some success in employing europium-labeled chelate as a marker group in homogeneous methods (Soini E et al. U.S. Pat. No. 4,587,223). In that case we used a chelating ligand bound covalently to insulin (immune reactant), this being a ligand of the type that is unable to absorb and transfer light energy to a chelated lanthanide ion but forms very stable lanthanide chelates. Thus, the chelate of covalently bound ligand plus lanthanide ion ($Eu^{3+}$) exhibited fluorescence only if additional ligands were present which were capable of absorbing and transferring light energy to the lanthanide ion. It has not yet been possible to provide this type of lanthanide chelate in the form of a commercial product utilizing the homogeneous technique in conjunction with time resolved fluorescence spectroscopy. EP-A-195,143 (Example 19 pp 32–33, and claim 20) describes a homogeneous immunochemical method employing fluorescent lanthanide chelates. It is not clear from the text whether or not recourse has been had to time-resolved fluorescence spectroscopy. The said example is only a model experiment carried out in the absence of all such disturbing components that may be present in any normal sample.

In the Soini et al. specification (U.S. Pat. No. 4,374,620) there is some speculation—without experimental support—that the immune reaction between lanthanide chelate labeled reactant and its immunological counterpart might affect the fluorescence signal.

OBJECT OF THE INVENTION

The object of the invention is to provide improved homogeneous immunochemical assays of the type set forth in the introduction of the present specification. With the aid of the invention time-resolved fluorescence spectroscopy may be used for determining analyte concentrations of below $1\times10^{-4}$M. According to one main aspect of the invention a method is provided for stabilizing lanthanide chelates within the technical field contemplated, so that solely the analyte will affect the measurable delayed fluorescence. This aspect, thus, involves a neutralization of the negative effect on fluorescence that may be exerted by a major number of the substances occurring in a biological sample. According to a minor aspect of the invention, a method is provided which prevents water from quenching the fluorescence from lanthanide chelates.

THE INVENTION

The invention has substantially two characteristic features:
  (i) The ligand bound covalently to an immune reactant is to be capable of absorbing light energy which is transmissible to the chelated lanthanide ion so as to enable said ion to exhibit its characteristic ionic fluorescence.
  (ii) One or more fluorescence-modulating substances (modulators, e.g. proteins or detergents) which do not stem from the analyte-containing sample must be added to the reaction medium in an amount such and of a type such that the measurable fluorescence will not be affected by such fluorescence-affecting substances which are present in varying amounts in biological samples. As a consequence, the fluorescence actually measured will be a practically pure function of the analyte concentration in the reaction medium and thus also in the sample.

The term "reaction medium" refers to the medium in which the immune reactions and fluorescent assays are carried out. In addition to the modulator added and to the analyte, in conjunction with other substances entrained from the sample, the medium contains labeled immune reactant which may be an analyte analog or an antibody directed against the analyte, buffering components etc. One of the immune reactants added may be provided with appropriate energy-acceptor groups such as chelates of heavy metals (e.g. copper or chromium ions) in order to further increase any potential fluorescence inhibition caused by an immune reaction.

Lanthanide chelates

Lanthanide ions: As stated above these ions are selected from among $Eu^{3+}$, $Sm^{3+}$, $Tb^{3+}$ and $Dy^{3+}$.

Ligand: In view of the vast potential of lanthanide chelates as marker groups, information about a large number of compounds has been published during recent years. It has been contended that the compounds can be used to replace the previously employed beta-diketones. Attempts have been made to correlate the structures of various compounds with their ability to absorb and transfer light energy to a chelated lanthanide ion. The results have been somewhat ambiguous due to the fact that evidently every kind of modification of a ligand, and so also the coupling thereof to an immune reactant, will be apt to affect the fluorescence. Consequently experimental trials are always required for deciding whether or not a compound is suitable. From the point of view of spectroscopy it has been found that the ligand should contain an aromatic structure absorbing excitation energy at wavelengths within the range of 250–390 nm, desirably 300–350 nm. The ligand should have an excited triplet level sufficiently above the emitting level of the lanthanide ion. For an efficient energy transfer the aromatic structure should have heteroatoms such as nitrogen (e.g. pyridine-N or aromatic amine (Ar—$NH_2$) or oxygen (e.g. furan-O or phenolic hydroxyl). A heteroatom thus may either be part of or be directly bound to an aromatic ring or to a conjugated system of double or triple bonds. At the same time there should be further heteroatoms which together with one of said first-named heteroatoms are able to chelate a lanthanide ion so that then five- or six-membered rings will be formed. The ligand has to contain at least 6 and preferably at least 8 or 9 such chelating heteroatoms, and these may be selected from among oxygen (e.g. carboxyl, sulfonate, phosphate, phosphonate, ether, —N=O, C=O), nitrogen (e.g. primary, secondary or tertiary amine), phosphorus (e.g. phosphine or phosphine oxide) and sulfur (e.g. C=S). Compounds having the structure in question and their covalent coupling to various biologically active compounds are described in a number of patent publications and scientific articles (Travenol-Genentech Diagnostics, EP-A-195,413; HSC Research Development Corporation, EP-A-171,978; Kankare et al., EP-A-203,047; Hinshaw et al., EP-A-68,875; Mathis G et al., FR-A-2,570,703; and Bailey et al., Analyst 110 (1985) 603–4). As examples of specific groups of compounds may be mentioned pyridines such as 2,6-disubstituted pyridines which have a substituted ethynyl group in their 3-, 4- or 5-position and in which the substituents on the 2- and/or 6-positions comprise chelating heteroatoms at an appropriate distance from the pyridine nitrogen for forming, together with a lanthanide ion, the five- or six-membered rings mentioned above. Further examples are covered by the attached claims which constitute a part of this specification. In many cases it may be an important requirement that the conjugation of the ligand to the immune reactant is performed in such a manner that the conjugate will comprise a chain of at least five carbon atoms between the immune reactant and the aforesaid aromatic ring or a pi-electron system conjugated to that ring.

Modulator

The invention is based on the concept that a fluorescence-modulating substance (modulator) shall stabilize and protect the fluorescent lanthanide chelate employed as a covalent label, so that the lanthanide fluorescence will become dependent solely on the analyte concentration. The effect of variations in sample constituents other than analyte will become negligible.

The amount of modulator should be a functional excess over the (varying) amounts of fluorescence-affecting substances from the sample—for the purpose that the modulator added should efficiently prevent any such other substances from binding to the lanthanide chelate and thus affecting the fluorescence signal. However, it ought to be mentioned that too large an excess of modulator may have the result that the fluorescence turns out to be practically independent of the analyte concentration. The concentration optima depend i.a. on the affinity constants of the modulator and lanthanide chelate inter se and of the labeled immune reactant and its immunological counterpart inter se. The optima normally can be found in the concentration range 0,1–10 g modulator per liter.

From the above it is clear that the cooperation between the modulator och chelating ligand is complex. Pretrial experiments with different modulators and modulator concentrations are therefore required to determine the optimum conditions. See the experimental portion of this specification.

In the experiments we have made up to now we have preferred to use a modulator enhancing the fluorescence intensity from the free labeled immune reactant. The immune reaction will usually then result in a weakening of the fluorescence, and this type of modulator has thus provided the possibility of measuring the amount of free labeled reactant. If the labeled reactant is an analyte analog having an epitope in common with the analyte and if the amounts are chosen such that the analyte and its analog have to compete for an immunological counterpart directed against the epitope (i.e. an insufficient amount of the counterpart), then an increased analyte concentration will give an intensified fluorescence.

In other embodiments of the invention it may be possible to select modulators that decrease the fluorescence.

Examples of suitable modulators are macromolecular substances, such as proteins, and detergents.

It is a well known fact that proteins are capable of binding to aromatic structures, especially in low molecular compounds. Examples are albumin and globulins. The binding of the protein with the lanthanide chelate should preferably be of a non-immunochemical nature although this is not necessary. What is important here is that the protein must not bind too strongly to the analyte epitope to be utilized.

In view of the fact that serum samples contain large amounts of albumin it is a requirement for serum samples in general, in cases where albumin is employed as modulator, that the concentration of added albumin should not be more than 2–10 times the concentration of the albumin from the sample itself, the absolute amount depending on the extent to which the sample is diluted when the reaction medium is admixed with the sample. A valuable help for a person skilled in the art is knowing that the total protein content in serum amounts to 4–7%.

Detergents are compounds having a hydrophobic end and a hydrophilic end. They reduce surface tension and will form micelles when present in a sufficiently high concentration. The detergents used as modulator in the invention may be selected from among the non-ionic or ionic (anionic, cationic and amphoteric ones). Their molecular weights may exceed 1,000 or even 5,000 daltons. High molecular detergents may be able to more efficiently prevent the quenching effect of water. It is often practical that the detergent concentration exceeds the critical concentration of micelle formation.

Samples

The samples that may be used in the context of this invention are the same as those used in ordinary immunochemical assays. As examples may be mentioned urine, plasma, serum, CSF, lymph etc. The greatest advantages of the invention are obtained in the cases of samples containing large amounts and large variations of protein, e.g. serum and plasma.

Other additions to he reaction medium

The pH of the reaction medium is within such a range as is commonly employed in immunochemical assays. Too low a pH should be avoided as this would tend to cause dissociation of the lanthanide chelate. By rule of thumb, the pH should lie in the range of 6–9. A person skilled in the art knows how to choose an optimum pH with respect to the antigen-antibody pair to be employed and with respect to how the fluorescence of a given system will be affected by the pH. The reaction medium is buffered to the optimum pH in a manner known per se. Excepting the chelating ligand strongly complexing agents should be avoided as they would tend to promote dissociation of the lanthanide ion from the labeled reactant.

Analyte

The invention can potentially be applied to the finding of any and every biologically active organic compound which is capable of participating in biospecific affinity reactions. Results obtained up to now have shown that the invention is most suitable for haptens and other low molecular substances, e.g. those having molecular weights below 5,000 daltons. Examples are hormones which often have a non-peptide structure, as e.g. steroids. It is preferred to employ competitive techniques for antigens and haptens. Particularly great advantages are obtained with analyte concentrations below $10^{-4}$ mol/lit.

In contrast to the methodology of DELFIA the present invention enables non-separation simultaneous assays of two or more analytes. In this type of embodiments lanthanide chelates having different excitation or emission wavelength maxima are used as covalent labels.

The invention is defined by the attached claims and will now be illustrated by means of a number of non-limitative examples of the most preferred embodiments. The structure of the compounds produced are set forth on separate pages. All fluorescence measurements have been performed according to the time-resolved principle.

EXAMPLE 1

Production of activated thyroxine ($T_4$)

Activated N-hydroxysuccinimide ester of the monoamide of suberic acid with thyroxine was produced and coupled to various amino derivatives of fluorescent chelates. Di-succinimidylsuberate was produced in dry dioxane according to known methods (Anderson et al., J. Am. Chem.

Soc. 86 (1964), 1839–42. Pilch and Czech, J. Biol. Chem. 254 (1979) 3375–80) from suberic acid and N-hydroxysuccinimide in the presence of N,N'-dicyclohexylcarbodiimide. A white solid (m.p. 159° C.) was obtained upon crystallization in acetone-diethylether. The product obtained, disuccinimidylsuberate, was then reacted with thyroxine in dry dimethylformamide and in the presence of triethylamine so as to form the desired N-hydroxysuccinimide ester (=activated thyroxine).

$^1$H-NMR, 400 MHz, DMSO-$d_6$, : 1.05–2.05 (m, 10H), 2.59 (s,1H), 2.62 (t, 2H), 2.81 (s,4H), 3.06 (dd, 2H), 7.05 (s, 2H), 7.74 (s, 2H).

EXAMPLE 2

Production of activated triiodothyronine ($T_3$)

The N-hydroxysuccinimide ester of the monoamide of suberic acid With triiodothyronine ($T_3$) was prepared in a manner analogous to that described in respect of thyroxine.

EXAMPLE 3

Activation of steroids

N-hydroxysuccinimide esters of carboxylic acid derivatives from cortisol and progesterone were produced in dry dioxane by condensation of the said carboxylic acid derivatives and N-hydroxysuccinimide, the condensation agent employed being N,N'-dicyclohexylcarbodiimide. The carboxylic acid derivatives, i.e. cortisol-3-(O-carboxymethyl) oxime and progesterone-3-(O-carboxymethyl)oxide, were prepared with 3-(N-pyrrolidyl)enamine as intermediate (Janoski et al., Steroids 23 (1973), 49–64).

EXAMPLE 4

Labeling of progesterone

Activated progesterone from Example 3 was coupled to ligand (V) (chelated with $Eu^{3+}$) in a water-dioxane solution. After 3 hrs of stirring at 20° C. the product (VIII) could be precipitated with acetone and purified by means of TLC (acetonitrile-water, 4:1 v/v as the eluant).

In a similar manner the $Tb^{3+}$ chelate of ligand (II) was coupled to progesterone so as to form the conjugate (IX). Purification was performed by means of TLC (acetonitrile-water, 4:1 v/v).

EXAMPLE 5

Labeling of cortisol

Activated cortisol from Example 3 was coupled with the $Eu^{3+}$ chelate of ligand (V). Coupling was effected in dioxane-water, the product (X) then being purified by means of TLC.

In a similar manner the $Eu^{3+}$ chelate of ligand (VII) was coupled to activated cortisol from Example 3, and again in a similar manner the $Eu^{3+}$ chelate of ligand (V) was coupled to cortisol-21-hemisuccinate. The products obtained were (XI) and (XII), respectively.

EXAMPLE 6

Labeling of thyroxine Activated thyroxine from Example 1 was coupled to the $Eu^{3+}$ chelate of ligand (V) in dioxane-water, whereupon the product (XIII) could be purified by means of TLC. In a similar manner $Tb^{3+}$ chelate of ligand (I) was coupled to give product (XIV).

EXAMPLE 7

Labeling of triiodothyronine ($T_3$)

Activated $T_3$ from Example 2 was coupled to the $Eu^{3+}$ chelate of ligand (V) according to the same method as that described for thyroxine. The product (XV) was purified by means of TLC.

EXAMPLE 8

Relative fluoroscence of labeled compounds produced

Protein and detergent effects on the fluorescence outputs of the labeled compounds were tested in a buffer (50 mmol/liter Tris-HCl, pH 7.75, containing 9 g/liter NaCl and 0.5 g/liter $NaN_3$). The results are set forth in Table I. In addition to detergents, other factors influencing the relative fluorescence are the buffering ions employed and the pH chosen. Proteins are very special items in this context inasmuch as their effects are more potent and may easily override the effects of other modulators. Therefore if a system contains proteins as e.g. in cases of assays for analytes in plasma, serum, urine and similar samples, modulation of the fluorescence signal is preferably carried out with protein.

TABLE 1

Fluorescence yields of different hapten-chelate conjugates in buffers containing albumin or detergents.

| | Tris-HCl buffer + | | | | |
|---|---|---|---|---|---|
| Conjugate | cps | BSA 0.5% cps | Tween ® 20 0.1% cps | SDS 0.1% cps | Cetylpyridine 0.1% cps |
| VIII | 9 600 | 17 600 | 9 900 | 8 200 | 18 600 |
| IX | 3 200 | 22 500 | 111 000 | 14 100 | 4 000 |
| X | 8 500 | 119 300 | 10 300 | 7 700 | 12 200 |
| XI | 920 | 3 600 | 880 | 9 500 | 1 190 |
| XII | 2 200 | 4 500 | 2 300 | 2 270 | 3 200 |
| XIII | 370 | 10 600 | 1 200 | 400 | 1 050 |
| XIV | 2 040 | 40 510 | 2 060 | 2 960 | 450 |
| XV | 430 | 17 400 | 1 370 | 350 | 1 200 |

EXAMPLE 9

Effect of protein concentration on fluorescence of the conjugates

Figure 1:
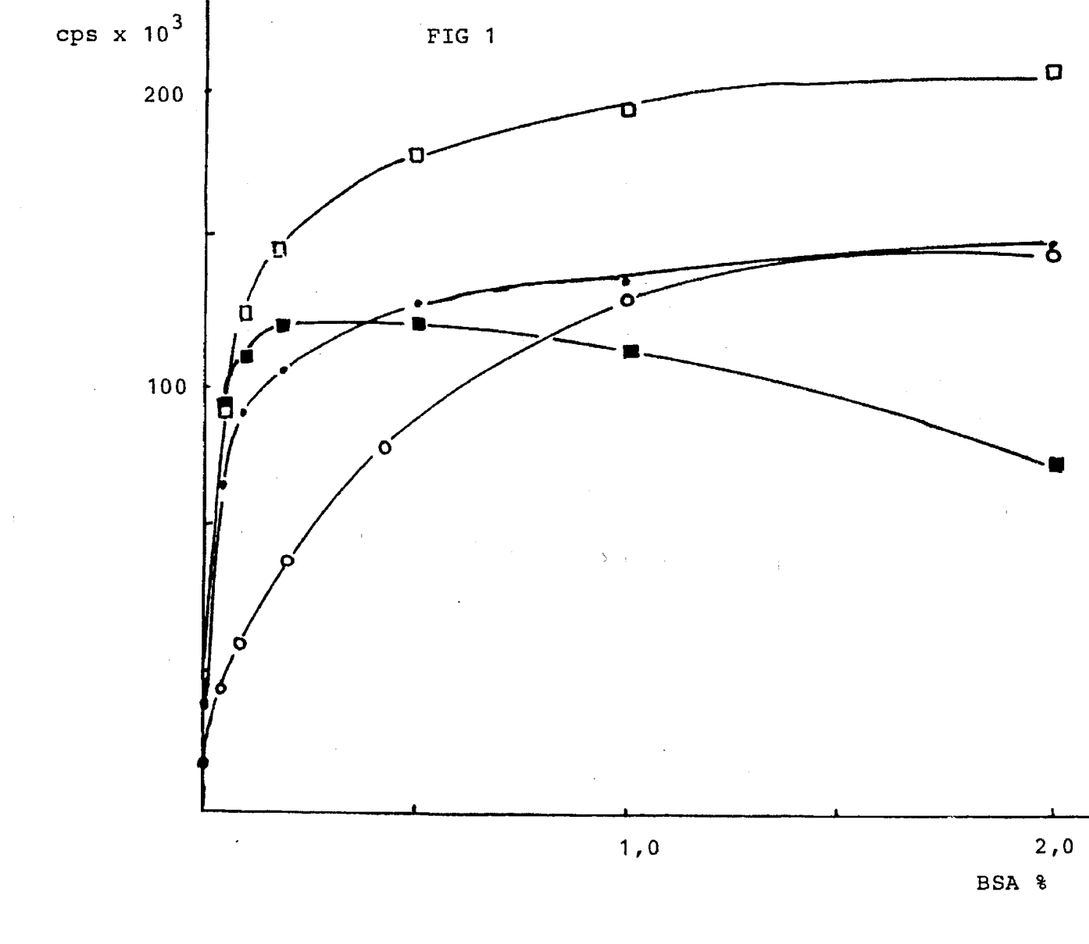
FIG. 1: Fluorescence of some $Eu^{3+}$ and $Tb^{3+}$ labeled biologically active compounds as a function of protein concentration (BSA). The conjugates tested were $Eu^{3+}$ labeled cortisol (X) (○), $Eu^{3+}$ labeled $T_4$ (XIII) (□), $Tb^{3+}$ labeled $T_4$ (XIV) (■), and $Eu^{3+}$ labeled $T_3$ (XV) (.). Conjugate concentrations were about 10 nmol/liter.

The increase of fluorescence in conjugates (X), (XIII), (XIV) and (XV) as a function of protein concentration is shown in FIG. 1. Although the conjugates exhibited different degrees of affinity for the added protein an amount of 0.5–2% (w/v) was sufficient to give an approximately maximal fluorescence.

EXAMPLE 10

Inhibitory effect of monoclonal anti-thyroxine antibodies on the fluorescence from labeled thyroxine (XIII)

Figure 2:
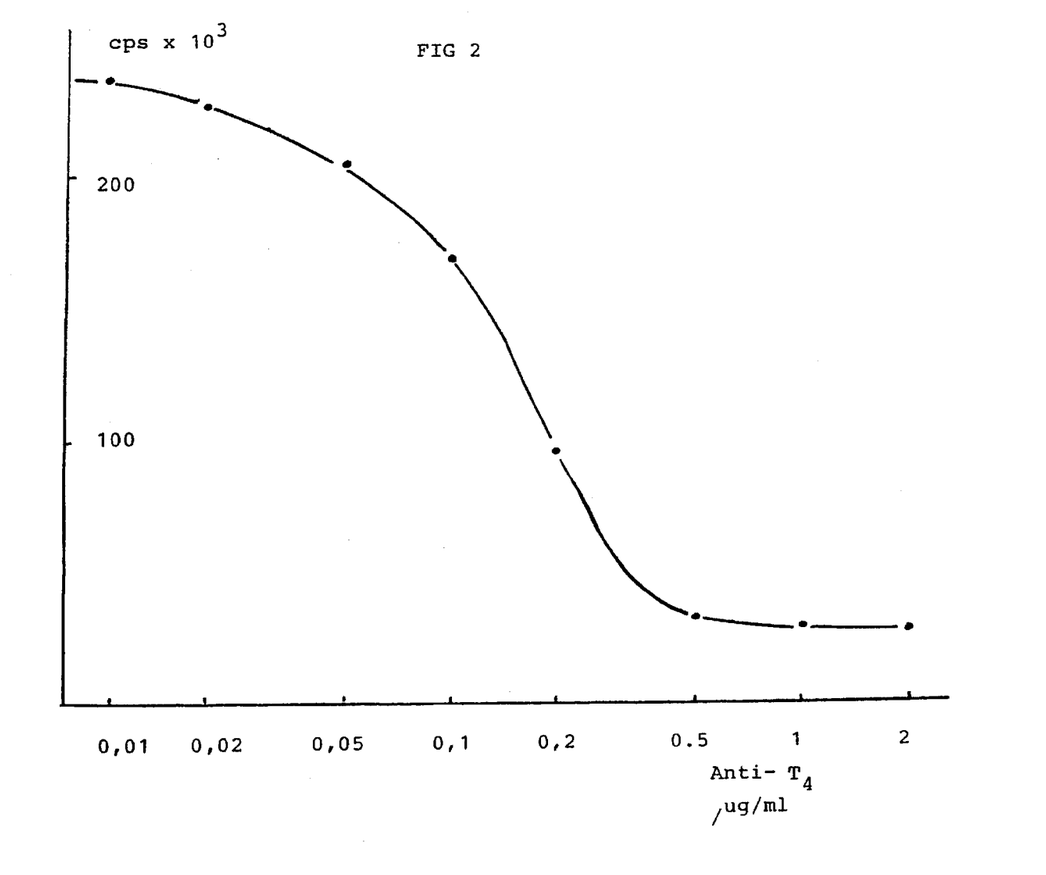
FIG. 2: Anti-$T_4$ antibody dilution curve. Inhibition as obtained by titration of u labeled $T_4$ (XIII) with anti-$T_4$ antibodies. The titration was performed in a succinate buffer (0.1 mol/liter, pH 6.0, in the presence of 1% (w/v) BSA.

Monoclonal anti-thyroxine antibodies were incubated with labeled thyroxine (XIII), the incubation being performed in a succinate buffer (0.1 mol/liter., pH 6.0) in the presence of 2% BSA (w/v). The antibodies caused inhibition of the fluorescence as shown in FIG. 2.

EXAMPLE 11

Dose-response curve of thyroxine

Figure 3:
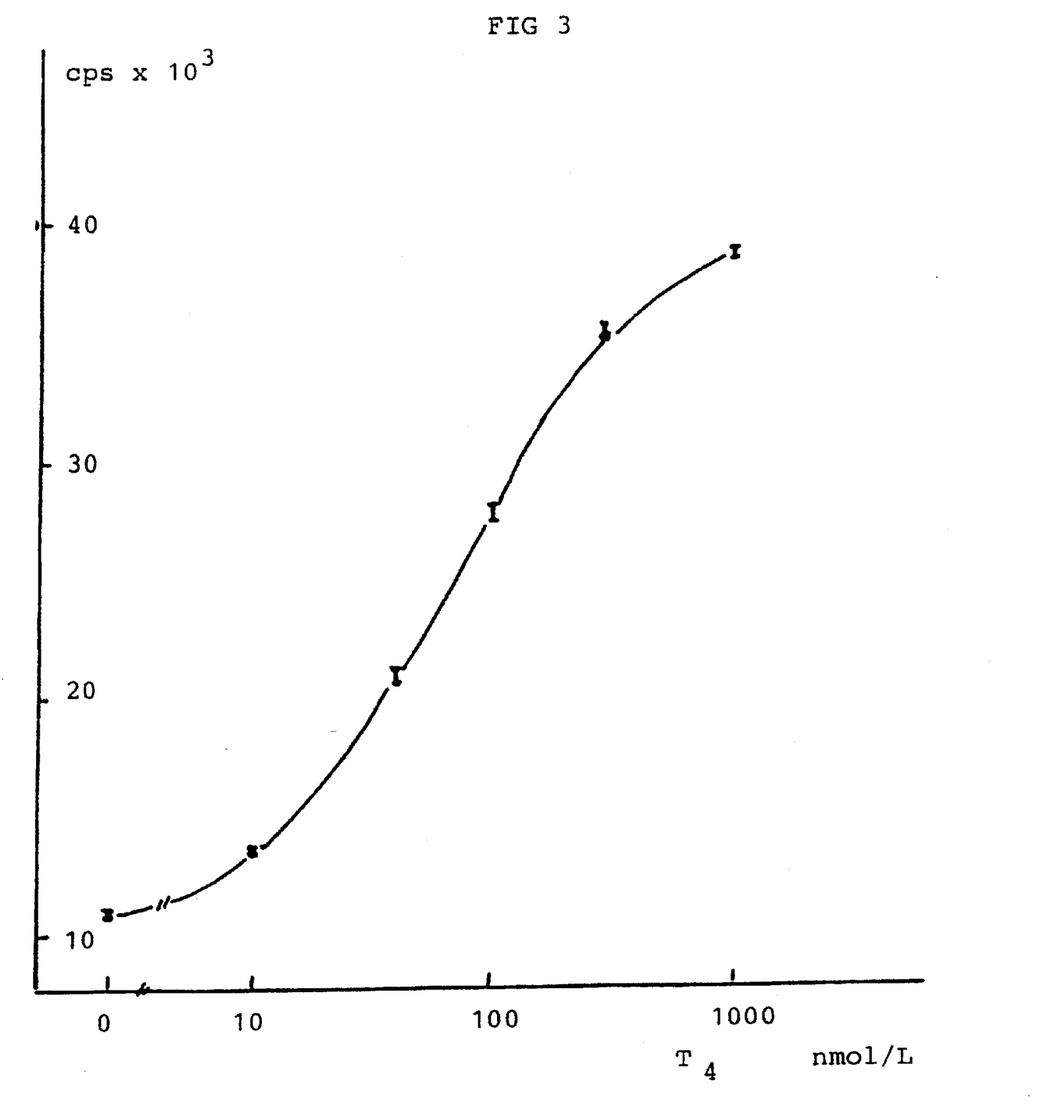
FIG. 3: Dose-response curve of a homogeneous $T_4$ TR-FIA (=time-resolved fluorescence immunoassay).
Figure 4:
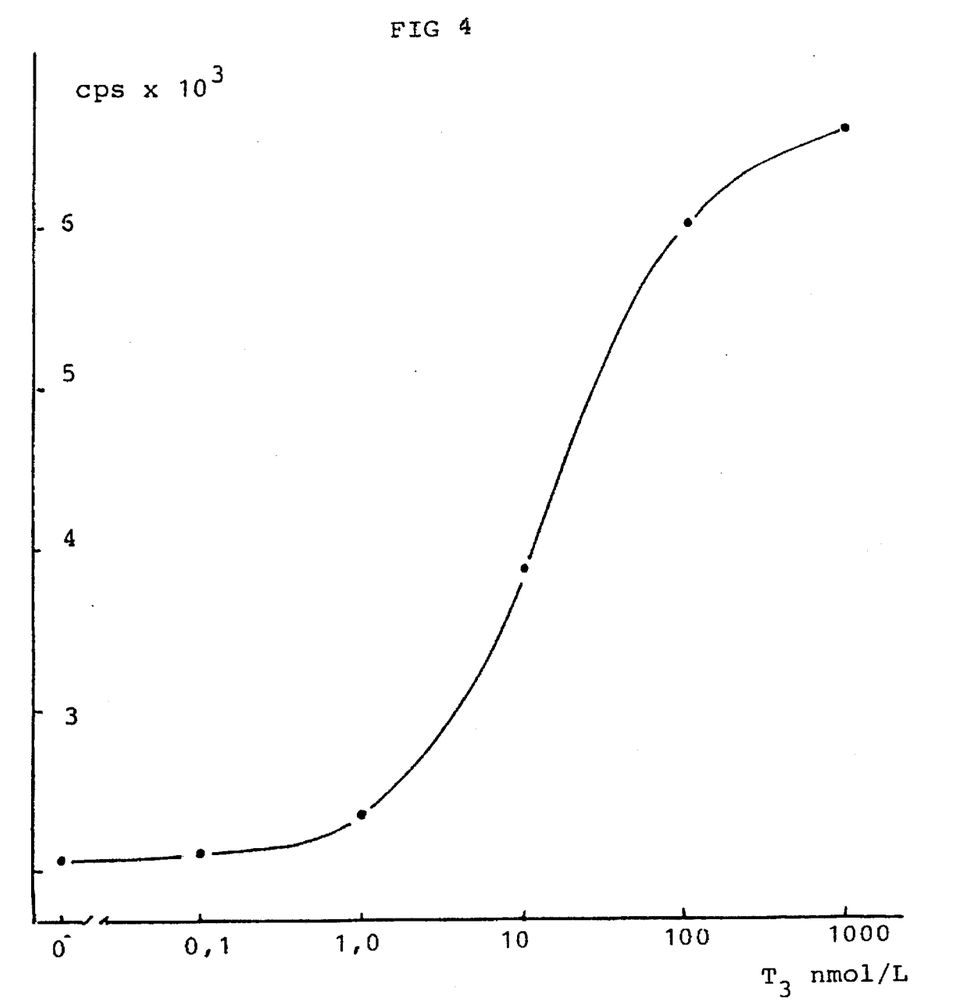
FIG. 4: Dose-response curve of a homogeneous $T_3$ TR-FIA.

The buffer system and labeled thyroxine were the same as in Example 10. An amount of anti-thyroxine antibody was used such that the antibody inhibited 80% of the fluorescence intensity. 20 μl standards (0, 10, 50, 100, 500 and 1,000 nmol/liter) diluted in normal human serum that was free of $T_4$ were added to 200 μl assay-buffer (succinate, 0.1 mol/liter pH 6.0, containing 0.9% NaCl (w/v), 0.2% merthiolate (w/v), 5 nmol/liter $Eu^{3+}$ labeled thyroxine and 2% BSA (w/v)) containing antibodies. The change in the intensity of the fluorescence as a function of added thyroxine was measured after 30 minutes of incubation at +20° C. Dose-response curve, see FIG. 3.

EXAMPLE 12

Dose-response curve of triiodothyronine

In a way similar to that described in Eample 11, a dose-response curve could be constructed for triiodothyronine. 200 μl of buffer (0.1M succinate. pH 6.0, containing 2% BSA, 0.2% thiomersal, 2% glycerol), 1 nM $Eu^{3+}$ labeled triiodothyronine (XV) and polyclonal anti-$T_3$ antiserum were incubated with 20 μl of $T_3$ standards. Incubation was allowed to proceed for 1 hour at room temperature. A dose-response curve could be constructed by means of measuring the intensity of the fluorescence as a function of the amount of added $T_3$.

EXAMPLE 13

Dose-response curve of cortisol

In a manner analogous to that of the preceding examples with $T_4$ and $T_3$, dose-response curves for a homogeneous system were constructed for cortisol with the aid of the $Eu^{3+}$ conjugates (X), (XI) and (XII). The buffer systems employed were: Tris-HCl buffer, 5 mmol/liter., pH 7.75, containing 9 g/liter NaCl, 0.5 g/liter $NaN_3$ and 5 g/liter BSA, or phtalate buffer, 0.1 mol/liter., pH 5.5, containing 9 g/liter NaCl and 5 g/liter BSA. Concentrations of $Eu^{3+}$-labeled cortisol varied between 1 and 10 nmol/liter. Incubation for 15–20 minutes at +20° C.

EXAMPLE 14

Labeling of anti-$T_4$ antibodies with $Cu^{2+}$ and $Cr^{3+}$

Purified anti-$T_4$ IgG was labeled with $Cu^{2+}$ or $Cr^{3+}$ respectively by means of a bifunctional chelating reagent, p-isothiocyanate benzyl-DTTA (see further in EP-A-139, 675). Labeling was carried out in a carbonate buffer, 50 mmol/liter., pH 9.8, with a 100-fold molar excess of the reagent chelated with $Cu^{2+}$ or with $Cr^{3+}$. The labeled antibodies were purified from starting material by means of gel filtration (Sephadex G50, 1,5×30 cm).

EXAMPLE 15

Figure 5:
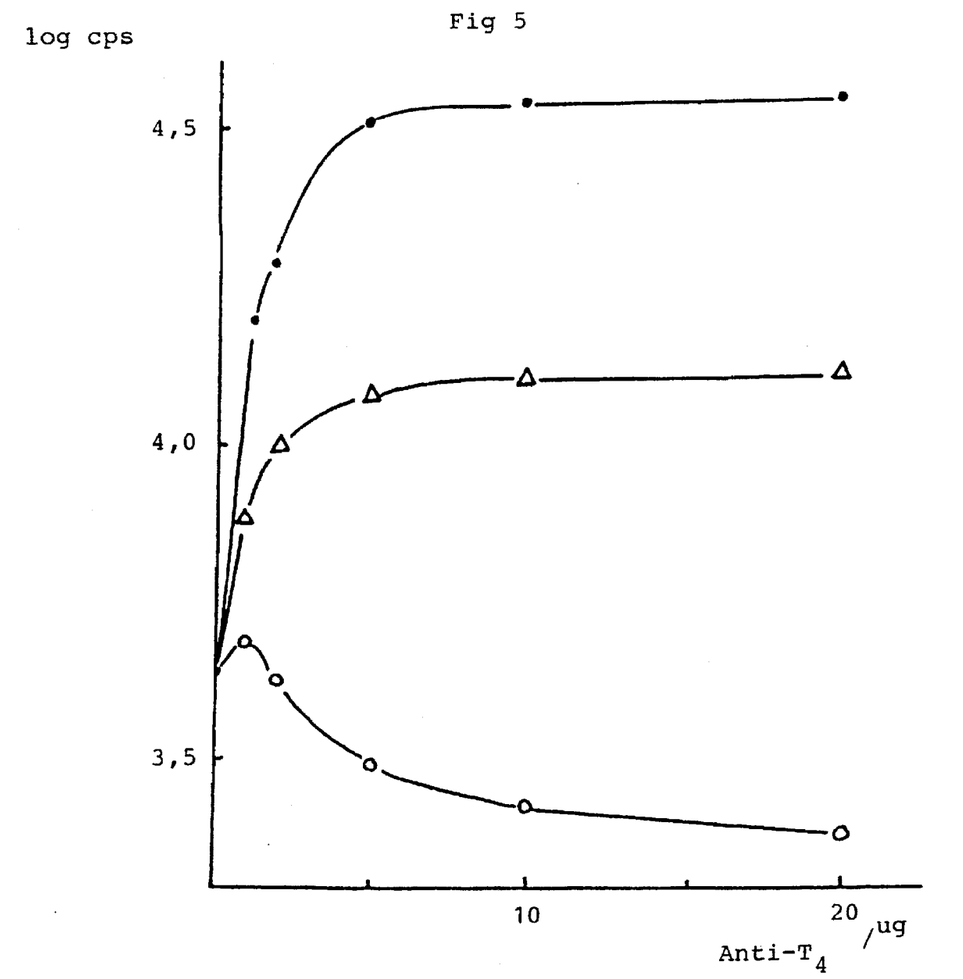
FIG. 5: Effect of nonlabeled (.), $Cu^{2+}$ labeled (○) and $Cr^{3+}$ labeled (Δ) antibodies on the fluorescence from $Eu^{3+}$ labeled $T_4$ (XIII) in a buffer not containing protein.

Inhibition of fluorescence from labeled thyroxine by means of energy transfer to $Cu^{2+}$ or $Cr^{3+}$ Fluorescence inhibition due to antibody binding to analyte could be reinforced with the aid of suitable energy acceptors, for example heavy metals bound to the antibodies. An increase in fluorescence could be observed when $Eu^{3+}$ labeled $T_4$ (XIII) was subjected to titration with unlabeled antibodies in a buffer that did not contain any other proteins (FIG. 5) This increase could be partially suppressed if $Cr^{3+}$ labeled or $Cu^{2+}$ labeled antibodies were employed (FIG. 5).

EXAMPLE 16

Assay of estrone-3-glucuronide in urine

During the priority year the invention has been applied to this analyte. Modulator: BSA 5 g/liter.

Structural formulae of synthesized compounds
Compounds (I) to (VII):

| Compound | $R^1$ | $R^2$ |
|---|---|---|
| I | H | $CONHCH_2CH_2NH_2$ |
| II | H | $CH_2NH_2$ |
| III | $NH_2$ | H |
| IV | $NH_2$ | $CH_2NH_2$ |
| V | $NH_2$ | $COCH_2CH_2NH_2$ |
| VI | $NH_2$ | $CONHCH_2CH_2CH_2CH_2CH_2CH_2NH_2$ |
| VII | OH | $CONHCH_2CH_2NH_2$ |

Structural formulae of synthesized compounds
Compounds (I) to (VII):

In formulae VIII to XV
R = Methyl
Ac = Acetyl

Chelated metal ion as set forth in the Examples (VIII)

(IX)

(X)

(XI)

Structural formulae of synthesized compounds
Compounds (I) to (VII):

(XII)

(XIII)

(XIV)

(XV)

We claim:

1. In the method for a homogenous biospecific affinity assay for determining the content of an analyte in a biological sample, said assay being carried out in an aqueous reaction medium by means of a biospecific affinity reactant labelled with a lanthanide chelate in which a lanthanide ion capable of exhibiting ionic fluorescence is chelated by a ligand bound covalently to the reactant, and said fluorescence being measured by means of time-resolved fluorescence spectroscopy, the improvement comprising that (i) the lanthanide chelate formed by the lanthanide ion and the covalently bound ligand exhibits fluorescence, and that (ii) a fluorescence modulator is added to the reaction medium in an amount so that the lanthanide fluorescence as measured from the medium becomes correlated to the analyte concentration therein, and effects on the lanthanide fluorescence from sample constituents other than analyte become negligible.

2. Method according to claim 1 wherein the analyte to be assayed has a concentration below $10^{-4}M$ in the reaction medium.

3. In the method for homogenous biospecific affinity assay for determining the content of an analyte in a biological sample, said assay being carried out in an aqueous reaction medium by means of a biospecific affinity reactant labelled with a lanthanide chelate containing a lanthanide ion capable of exhibiting ionic fluorescence and selected from the group consisting of $Eu^{3+}$, $Tb^{3+}$, $Sm^{3+}$ and $Dy^{3+}$, said ion being chelated by a ligand covalently bound to the reactant and said fluorescence being measured by means of time-resolved fluorescence spectroscopy, the improvement comprising that (i) the chelate formed between the covalently bound ligand and the lanthanide ion is fluorescent with a ligand structure which contains a chelating heteroatom having a free electron pair, said heteroatom being selected from the group consisting of nitrogen, oxygen, phosphorus and sulphur and being bound within the ligand in a manner such that the free electron pair is capable of delocalizing to a conjugated system of pi-bonds, and (ii) a fluorescence modulator is added to the reaction medium in an amount so that the fluorescence from the lanthanide chelate as measured from the medium becomes correlated to the analyte concentration therein and effects on lanthanide fluorescence from sample constituents other than analyte become negligible.

4. Method according to claim 3 wherein said analyte to be assayed has a concentration below $10^{-4}M$ in the reaction medium.

5. Method according to claim 3 wherein said fluorescence modulator is a protein.

6. Method according to claim 5 wherein said protein is selected from the group consisting of an albumin and a globulin.

7. Method according to claim 5 wherein said fluorescence modulator is an albumin.

8. Method according to claim 3 wherein said fluorescence modulator is a detergent selected from the group consisting of anionic, cationic, neutral and amphiphilic detergents.

9. Method according to claim 3 wherein said reactant labelled with the fluorescent lanthanide chelate is a hapten.

10. Method according to claim 3 wherein the concentration of said added fluorescence modulator in the medium is within 0.1–10 g per liter.

11. A method according to claim 1 wherein said biological sample is selected from the group consisting of plasma and serum samples.

12. A method according to claim 3 wherein said biological sample is selected from the group consisting of plasma and serum samples.

13. In the method for homogenous biospecific affinity assay for determining the content of an analyte in a biological sample, said assay being carried out in an aqueous reaction medium by means of a biospecific affinity reactant labelled with a lanthanide chelate containing a lanthanide ion capable of exhibiting ionic fluorescence and selected from the group consisting of $Eu^{3+}$, $Tb^{3+}$, $Sm^{3+}$ and $Dy^{3+}$, said ion being chelated by a ligand covalently bound to the reactant and said fluorescence being measured by means of time-resolved fluorescence spectroscopy, the improvement comprising that for a biological sample selected from the group consisting of plasma and serum samples, (i) the chelate formed between the covalently bound ligand and the lanthanide ion is fluorescent with a ligand structure which contains a chelating heteroatom having a free electron pair, said heteroatom being selected from the group consisting of nitrogen, oxygen, phosphorus and sulphur and being bound within the ligand in a manner such that the free electron pair is capable of delocalizing to a conjugated system of pi-bonds, and (ii) a fluorescence modulator is added to the reaction medium in an amount so that the fluorescence from the lanthanide chelate as measured from the medium becomes correlated to the analyte concentration therein and effects on lanthanide fluorescence from sample constituents other than analyte become negligible.

14. Method according to claim 13 wherein said analyte to be assayed has a concentration below $10^{-4}M$ in the reaction medium.

15. Method according to claim 13 wherein said fluorescence modulator is a protein.

16. Method according to claim 15 wherein said protein is selected from the group consisting of an albumin and a globulin.

17. Method according to claim 15 wherein said fluorescence modulator is an albumin.

18. Method according to claim 13 wherein said fluorescence modulator is a detergent selected from the group consisting of anionic, cationic, neutral and amphiphilic detergents.

19. Method according to claim 3 wherein said reactant labelled with the fluorescent lanthanide chelate is a hapten.

20. Method according to claim 13 wherein the concentration of the added fluorescence modulator in the medium is within 0.1–10 g per liter.

* * * * *